United States Patent [19]

Pompei

[11] Patent Number: 5,292,347
[45] Date of Patent: Mar. 8, 1994

[54] METHOD AND APPARATUS FOR REGULATING BODY TEMPERATURE

[75] Inventor: Francesco Pompei, Boston, Mass.

[73] Assignee: Exergen Corporation, Newton, Mass.

[21] Appl. No.: 765,486

[22] Filed: Sep. 25, 1991

Related U.S. Application Data

[63] Continuation-in-part of Ser. No. 479,332, Feb. 13, 1990, abandoned.

[51] Int. Cl.⁵ .............................................. A61F 7/00
[52] U.S. Cl. .................................... 607/104; 607/110
[58] Field of Search ................................ 128/399–403, 128/379, 380, 203.16, 367, 368; 165/96

[56] References Cited

U.S. PATENT DOCUMENTS

| | | | |
|---|---|---|---|
| 1,982,405 | 12/1934 | Davis | 4/537 |
| 2,098,316 | 11/1937 | Sittler | 128/373 |
| 2,311,899 | 2/1943 | Marlowe | 4/536 |
| 2,458,901 | 1/1949 | Fields | 128/375 |
| 2,566,531 | 9/1954 | Nissenbaum | 128/368 |
| 2,694,206 | 11/1954 | Foster | 4/537 |
| 2,817,340 | 12/1957 | Cuvier | 128/373 |
| 3,051,180 | 8/1962 | Adams-Ray et al. | 128/402 |
| 3,074,410 | 1/1963 | Foster | 128/400 |
| 3,474,790 | 10/1969 | Benzinger . | |
| 3,581,570 | 6/1971 | Wortz | 128/736 |
| 3,739,144 | 6/1973 | Janson | 4/524 |
| 3,861,364 | 1/1975 | Greenfeld | 128/68.1 |
| 3,902,488 | 9/1975 | Sheppard | 128/367 |
| 4,314,138 | 2/1982 | Itoh | 4/537 |
| 4,572,188 | 2/1986 | Augustine et al. | 128/380 |
| 4,683,869 | 8/1987 | Wilcox | 126/204 |
| 4,747,408 | 5/1988 | Chuan-Chih | 128/379 |
| 4,793,352 | 12/1988 | Eichenlaub | 128/399 |
| 4,953,546 | 9/1990 | Blackmer et al. | 128/203.16 |

FOREIGN PATENT DOCUMENTS

| | | |
|---|---|---|
| 52363/86 | 6/1985 | Australia . |
| 207995 | 3/1960 | Austria . |
| 1489635 | 6/1965 | Fed. Rep. of Germany . |
| 1410981 | 7/1988 | U.S.S.R. . |

OTHER PUBLICATIONS

Patent Cooperation Treaty / International Search Report For: PCT/US 91/00970.
A. Low and H. Geothe, "Comparison Between Heat Loss and Heat Gain Through the Lungs and the Surface of the Body During Hypothermia and its Treatment," Int. Arch. Occup Eniron Health 45 (1980) pp. 231–249.

*Primary Examiner*—Mark S. Graham
*Attorney, Agent, or Firm*—Hamilton, Brook, Smith & Reynolds

[57] ABSTRACT

A patient's body temperature is regulated by using an enclosure to enclose a portion of the patient's body in an isolated environment. In accordance with one embodiment, the patient's entire body below his head is enclosed. Once enclosed, the patient is surrounded by heated vapor that is injected into the enclosure. The heated vapor condenses on the patient's skin to warm the patient quickly, efficiently and safely. This embodiment is well suited for the treatment of hypothermia patients. In accordance with alternative embodiments, only a portion of the patient's head is enclosed. In these embodiments, an enclosure is placed on the patient's head, and heated vapor is fed into the enclosure. Excess air and vapor are preferably dissipated by vents in the cap, whereas excess condensate is preferably absorbed by an absorbent layer provided in the cap. These embodiments are well suited for regulating a patient's body temperature in a surgical setting. Tympanic temperature is monitored and thus vapor dew point temperature is controlled to less than 47° C. but greater than tympanic temperature.

19 Claims, 4 Drawing Sheets

METHOD AND APPARATUS FOR REGULATING BODY TEMPERATURE

RELATED APPLICATION

This is a continuation-in-part of application Ser. No. 07/479,332 filed Feb. 13, 1990, abandoned.

BACKGROUND OF THE INVENTION

Adjusting and maintaining a person's body temperature using external means has proven to be a difficult task in many instances. One means of adjusting and maintaining body temperatures is to submerge the patient into a bath of water. The water temperature in the bath is chosen to properly adjust the patient's temperature. Although this technique has proven to be quite useful in many applications it is not particularly appropriate in many instances.

For example, this approach often does not fare well with hypothermia patients. In such cases, the patient is typically submerged in a very warm bath to raise the body temperature of the patient. The use of a water bath is, however, frequently impractical, for it requires the use of a bath tub of sufficient size to completely submerge a patient, and it also requires close regulation of water temperature. Furthermore, this approach is time consuming because time must be spent preparing the warm bath. In cases such as at sea when a person has fallen overboard, these impracticalities can prove to be quite costly.

Another situation where the use of a water bath is impractical for regulating body temperature is in a surgical environment. Operating rooms are most often maintained at fairly cold temperatures to aid in the comfort of the surgical personnel. Unfortunately, it is not typically desirable for the patient to be exposed to such cool temperatures. In colder temperatures, patients tend to bleed more profusely and many patients may become uncomfortably chilled by the cold. Thus, it is generally desirable to employ a means for keeping the patient warm in this chilled environment. The previously described approach of submerging the patient into a heated bath is highly impractical for warming patients in the surgical environment. Thus, there is a need for a more practical approach to maintaining the patient's body temperature at a satisfactory level during surgical procedures.

SUMMARY OF THE INVENTION

The present invention concerns a device for safely and quickly regulating a patient's body temperature. The device is comprised of an enclosure that encloses a portion of the patient's body in an isolated environment. Once the portion of the patient's body has been appropriately enclosed, heated vapor is generated. The vapor is mixed with air to produce a saturated mixture. This mixture is delivered into the isolated environment created by the enclosure. The vapor surrounds the portion of the patient's body that lies within the enclosure. Since the patient's body is cooler than the heated vapor, the vapor condenses causing heat carried by the vapor to be transferred to the patient's body. The net result is that the patient's body temperature is quickly, efficiently and safely regulated.

This device preferably also includes a temperature monitor for monitoring the patient's body temperature as the vapor and air mixture are being generated. A tympanic monitor which senses thermal radiation from the tympanic membrane is ideal for the temperature monitor. The monitored temperatures are preferably fed back to a control means that regulates the operation of the vapor generator. As soon as a desired body temperature is achieved, the vapor generation may be significantly reduced or halted. Moreover, if a given body temperature must be maintained, a constant monitoring capability is provided.

The vapor produced by the vapor generator is preferably a saturated mixture of water vapor and air. Water vapor is an ideal candidate because of the magnitude of heat transfer that occurs when it condenses and secondly, because of its great availability. The vapor and air mixture should be heated to a dew point temperature no greater than about 43° C. (110° F.) and certainly no higher than 47° C. to avoid tissue damage. At 43° C., the water vapor achieves a significant level of heat transfer without causing any harmful tissue damage. The critical parameter for minimizing tissue damage is the difference in temperature between the vapor and the patient. Since a small temperature difference is maintained by the present invention, tissue damage is unlikely. The high heat transfer coefficient obtained by using condensing vapor plays a critical role in maintaining this small temperature differential. To obtain that condensation, the dew point temperature of the vapor must be greater than the blood temperature and, more specifically, greater than tympanic temperature. Normal body temperature is about 37° C., but for lower skin temperatures dew point temperature of 30° C. may be appropriate.

There are two approaches of the invention that are of particular interest. In the first approach, the portion of the patient below the head is enclosed within the enclosure. To provide such an enclosure a body bag device may be utilized. The device is preferably non-porous so that the vapor is kept entirely within the enclosure. In addition to the features previously described, this embodiment also includes a recycling means for collecting condensation and air from within the enclosure. Since the condensation and returning air are already heated, they require less heating when recycled than was initially required. This particular embodiment is ideal for a quick and easy treatment of hypothermia patients.

The other approach is well suited for surgical applications. Instead of enclosing the entire body like the previous embodiment, this additional embodiment encloses only a portion of the patient's head. The water vapor surrounds an area of the patient's head and heats blood flowing through the patient's head. The heated blood then travels throughout the patient's body warming the rest of the patient's body. As a result, the entire body temperature of a patient may be regulated merely by heating the patient's head.

Because this embodiment is designed for use in a surgical environment it does not have a condensation and air return. The condensation and air become contaminated when exposed to the patient and, therefore, should not be recycled in a sanitary surgical environment. This embodiment relies on a condensation gathering means to remove excess condensation, rather than a condensation return. In addition, vents are provided to allow excess vapor to escape.

Both of these embodiments offer quick and efficient means of regulating a patient's body temperature. The hardware necessary for such embodiments is limited and cost effective. Furthermore, these embodiments do not cause harmful tissue damage.

DETAILED DESCRIPTION OF THE PREFERRED EMBODIMENT

The present invention provides a means of regulating body temperature. This strategy employed in the present invention has applications in surgical environments and in the treatment of hypothermic patients. Both of these embodiments rely on enclosing a portion of a patient's body and surrounding the enclosed portion with heated vapor. The heated vapor condenses on the patient to bring about heating of the enclosed portion of the patient and in some instances, of the patient as a whole. The primary benefits of this approach are that it is quick; it does not cause harm to tissue exposed to the heated vapor; and it is very efficient.

Figure 1:
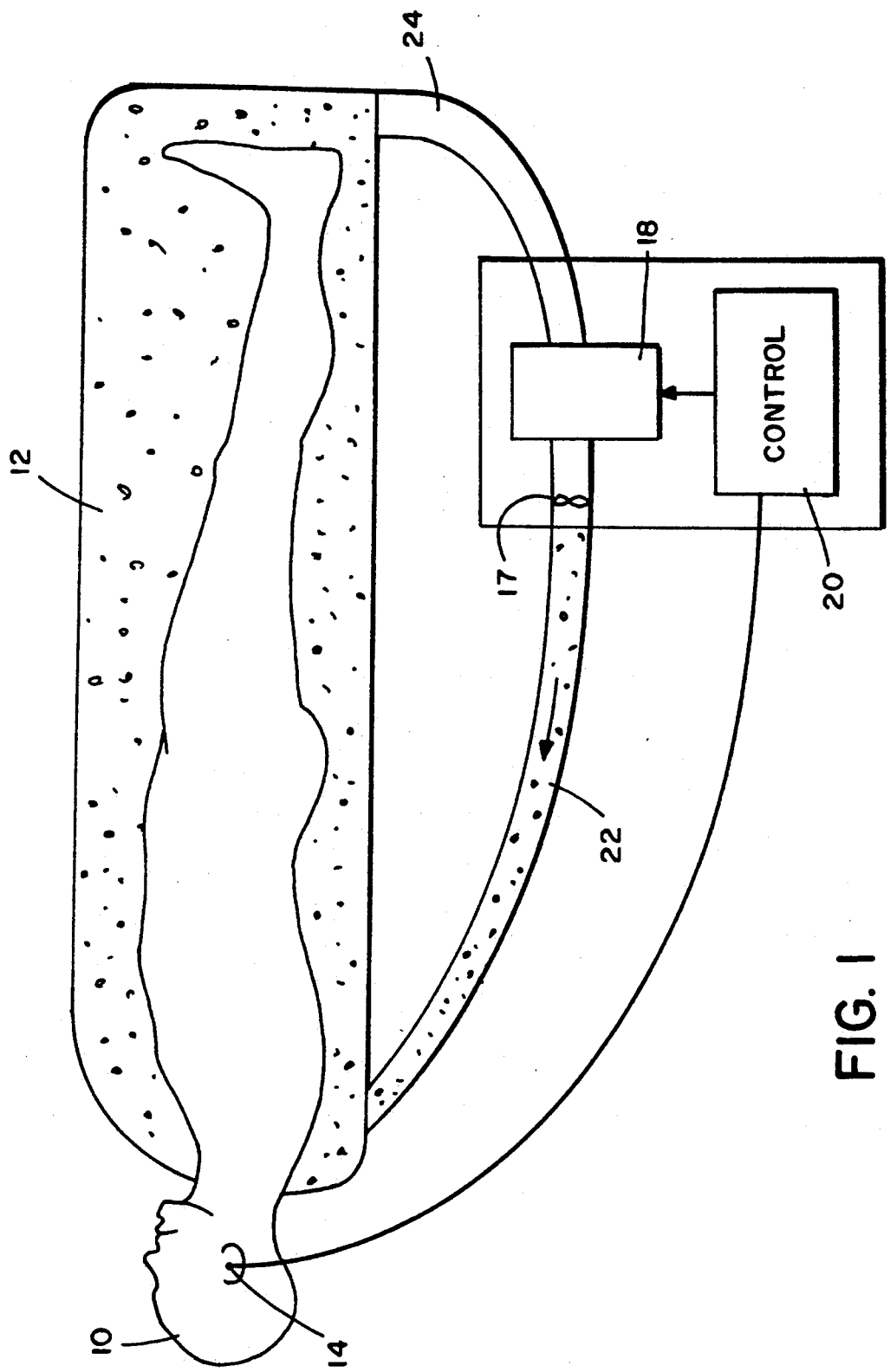
FIG. 1 depicts a first embodiment of the present invention ideal for use with hypothermia patients.

FIG. 1 depicts the first embodiment of the present invention. This embodiment is ideally suited for treating patients that are suffering from hypothermia. In accordance with this embodiment, the hypothermic patient 10 is placed inside an enclosing body bag 12. This body bag 12 covers the patient 10 from the head down. Portions of the patient's neck are likely to be exposed. The enclosing body bag 12 provides an enclosure that is non-porous and that isolates the patient 10 from the surrounding environment. The material is preferably made from a thermally insulative material so that heat inside the enclosure does not escape to the surrounding environment.

Once the patient 10 is properly placed within the enclosing body bag 12, a tympanic monitor 14 is placed in the patient's ear. A preferred monitor is disclosed in U.S. patent application Ser. No. 07/666,744. The tympanic monitor 14 determines the temperature at the patient's tympanic membrane. Research has indicated that such a measurement is an extremely accurate indicator of the patient's core temperature. The core temperature is widely regarded as the best available measurement of true body temperature. The tympanic monitor 14 is coupled to a controller 20 of a vapor generator 18. The vapor generator 18 is utilized to generate heated vapor that is injected along with air as a saturated mixture into the enclosing body bag 12. In particular, vapor mixture produced by the vapor generator 18 travels through a conduit 22 into the enclosing body bag 12. The vapor mixture is distributed throughout the enclosing body bag 12 so as to surround the patient 10. Because the temperature of the heated vapor is higher than the temperature of the patient 10, condensation occurs at the patient's skin. This condensation brings about heat transfer from the heated vapor to the patient's body 10. The resulting heat transfer produces a quick and efficient increase in the patient's body temperature. A temperature of about 110° Fahrenheit provides sufficient heat transfer without injury.

A controller 20 directs the activity of the vapor generator 18. The vapor generator 18 responds to the body temperature measurements sent from the tympanic monitor 14. Specifically, it adjusts the temperature of the air/vapor mixture that is being produced. Circulation of the vapor and air is aided by a fan 17 provided within the vapor generator 18.

The vapor generator 18 operates by bubbling hot air through a volume of water. The bubbling brings about evaporation of the water into the air. Sufficient water and air interface, in area and time, should be provided so that the air is fully saturated with water (i.e. 100% relative humidity). Less than fully saturated will provide the required condensation so long as the dew point of the vapor is greater than the blood temperature. The temperature of the air that is bubbled through the water and/or the temperature of the water may be adjusted to produce a mixture of water and air having a suitable temperature (i.e. 43° C.) for application to the patient. An alternative approach that may be adopted by the vapor generator 16 is to generate steam and to mix the steam with air to produce a fully saturated mixture of air and vapor having a suitable temperature. It should be noted that each approach is equally viable, and both are intended to be embodied within the present invention.

As mentioned above, the exposure of the heated vapor to the patient 10 results in a certain amount of condensation. This embodiment provides a means for gathering the condensation so that it may be recycled by the vapor generator 18. Specifically, the patient 10 is preferably oriented at a slight slope relative to the horizontal plane so that the condensation and air flow towards the condensation and air return 24. The resulting condensate and air are already heated to some extent and, thus, do not need to be heated as greatly when they are recycled. They travel via the return 24 to the vapor generator 16 wherein the condensate passes through the heat generator 18 to be heated and vaporized. The heated air continues along to the conduit 22 where it, once again, entrains additional heated vapor. The inclusion of the condensation and air return 24 increases the efficiency of the system. For reasons of contamination control, the system could be constructed without condensate or air return, by providing suitable venting for spent air/vapor mixture, and suitable condensate storage or drainage.

Benefits provided by this embodiment include that it is quicker than other embodiments. The vapor can be generated essentially instantaneously, whereas in the water bath strategy time is wasted in preparing the warm bath. Secondly, because this embodiment utilizes a tympanic monitor 14 with feedback and because the heat delivered by the vapor can be quickly controlled, this invention is a far more controlled strategy than mere submergence in a water bath.

The second approach of the present invention concerns a body temperature regulating means that maintains a patient's body temperature without a body bag. This particular embodiment is designed for use in a surgical environment. All of the components of this embodiment can be readily sterilized.

Figure 2:
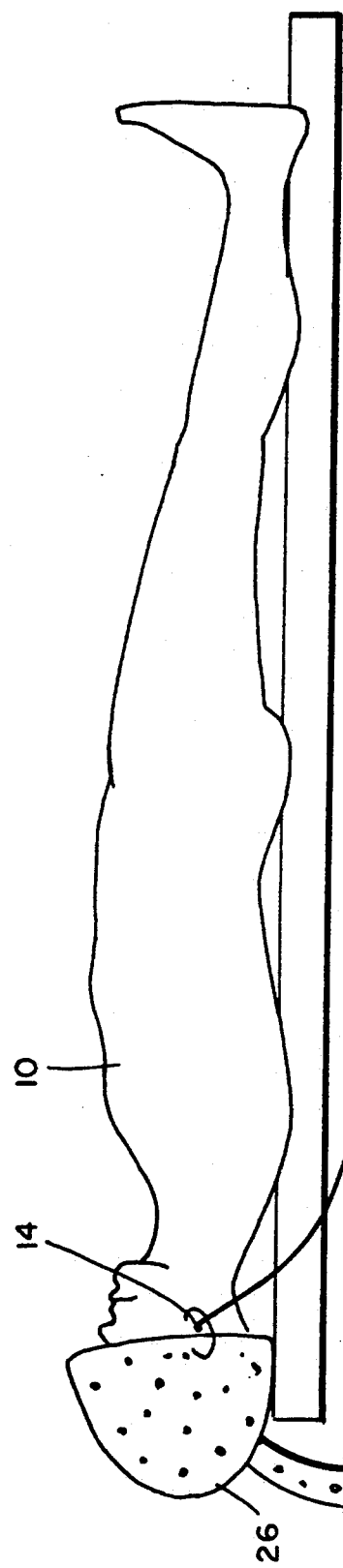
FIG. 2 depicts a second embodiment of the present invention that is ideal for use in a surgical environment.
Figure 3:
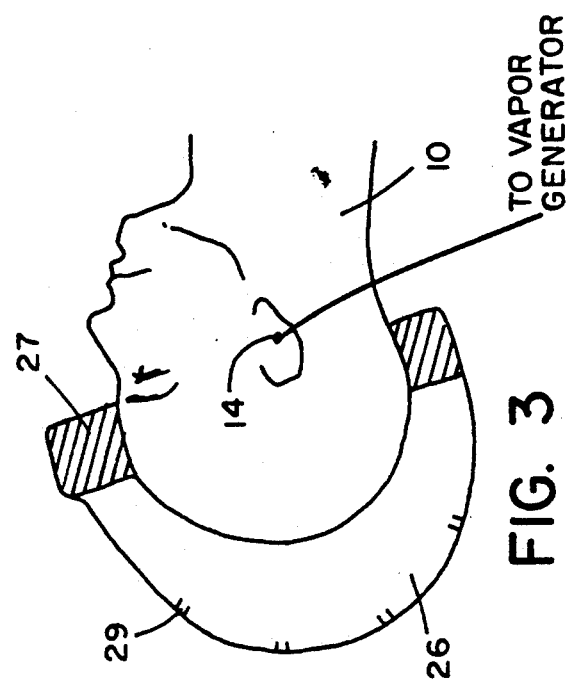
FIG. 3 shows a cross-sectional view of the cap used in the embodiment of FIG. 2.

In the embodiment of FIGS. 2 and 3, instead of entirely encapsulating the patient 10 with an enclosing body bag 12, a cap 26 is provided to cover the top surface of the patient's head. It is similar to its enclosing body bag counterpart in that it isolates a portion of the patient's body. It is also similar in use of the vapor generator 18. The heated vapor mixture is forwarded to the cap 26 via a conduit 22. The system is designed so that the vapor generator 16 can be placed in close proximity to the patient 10 in a surgical environment.

The system maintains a patient's body temperature during a surgical procedure. The cap 26 is placed on the patient 10 at the initiation of a surgical procedure. A tympanic monitor 14 is inserted into the patient's ear to furnish continuous data regarding the patient's body temperature. Like the previously described embodiment, the tympanic monitor 14 is coupled to the controller 20 of the vapor generator 18. This feedback is especially important in the surgical environment where it is desirable to maintain a steady body temperature.

This embodiment, however, does not have the condensation and air return 24. Exposure to the patient's body contaminates the condensation and air. It is, therefore, undesirable to recycle the contaminated condensation and air back through the vapor generator 18 because the recycling could contaminate the vapor generator 18.

Although the condensation air return 24 is not utilized in this embodiment, there are still certain features provided in this embodiment that address the issues of excess condensation and air. To remove unwanted condensation, a liquid collector may be provided within the cap 26. A primary candidate for such a collector is an absorbent band 27 of material as shown in FIG. 3 filled with an absorbent gel. As condensation begins to accumulate on the patient's head, the absorbent band 27 soaks up the condensation. Preferably, an absorbent material which in the presence of moisture becomes a dry gel is provided in the band 27. Such material is currently employed in products such as baby diapers (e.g. in Ultra-Pampers Plus ®). The gel filled material adequately removes the condensation because only a small amount of liquid (i.e. on the order of 8 ounces) need be vaporized and condensed to transfer significant amounts of heat, on the order of 500 BTUs. With respect to excess air and vapor, they are allowed to escape through vents 29 provided in the cap 26.

Figure 4A:
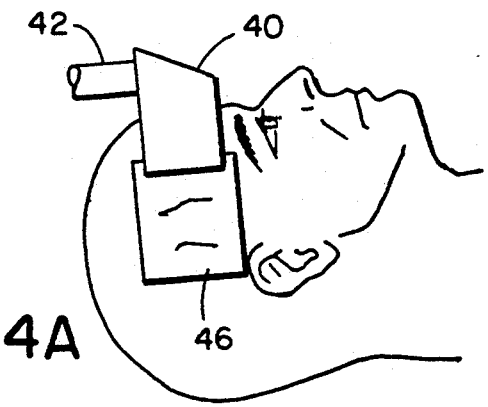
FIG. 4A illustrates a third embodiment of the invention which is also ideal for use in a surgical environment.
Figure 4B:
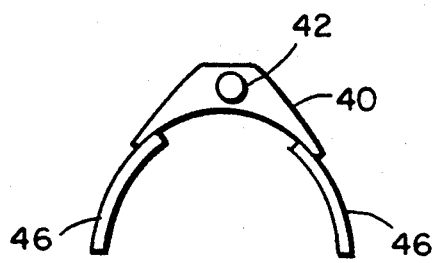
FIG. 4B is an end view of the device of FIG. 4A.
Figure 4C:
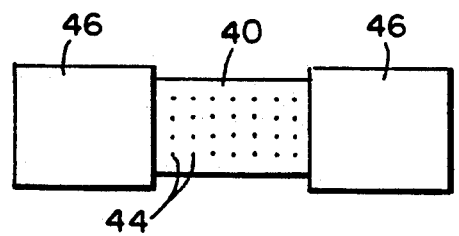
FIG. 4C is a bottom view of the device of FIG. 4A.

FIGS. 4A-4C illustrate an alternative embodiment particularly suited to the surgical environment. In this embodiment, only the forehead is heated. The vapor is directed through a supply tube 42 to a manifold 40 having a lower surface contoured to fit over the forehead as a vapor enclosure. That lower surface is perforated with small vapor spray holes 44. Due to the high efficiency of the condensation heat transfer mechanism, only a small amount of vapor flow is required, so small holes are preferred to restrict flow and thus minimize the vapor generation requirements. To collect the condensate, pads of absorbent material extend from beneath the ends of the manifold alongside the patient's head. Any condensation on the forehead flows into the two absorbent pads 46. The pads also serve to support the manifold 40 above the forehead to permit spraying of the vapor onto the skin. Any noncondensed vapor passes freely from under the spaced manifold.

The surgical embodiments utilize the fact that a great amount of heat transfer naturally occurs through the human head. In particular, there is a great deal of blood flow through the human head, and the blood that flows through the head is in close thermal communication with the external environment. Typically, about 40% of the heat transferred from the body is through the head, so a much more compact heat transfer unit may be used. On the other hand, if heat is applied to the human head, it is absorbed by the blood that is flowing through the head. The resulting heated blood travels throughout the rest of the patient's body, and keeps the patient's body at a standard temperature. With heating, the natural response of the body is to increase blood flow and, thus, further improve heat transfer and distribution. By using such a strategy, the patient is kept warm without the problems of interference with the surgical procedure that have traditionally confronted medical personnel. Furthermore, the strategy is very efficient and requires minimal amounts of water to generate sufficient vapor to maintain the patient's body temperature.

Figure 5:
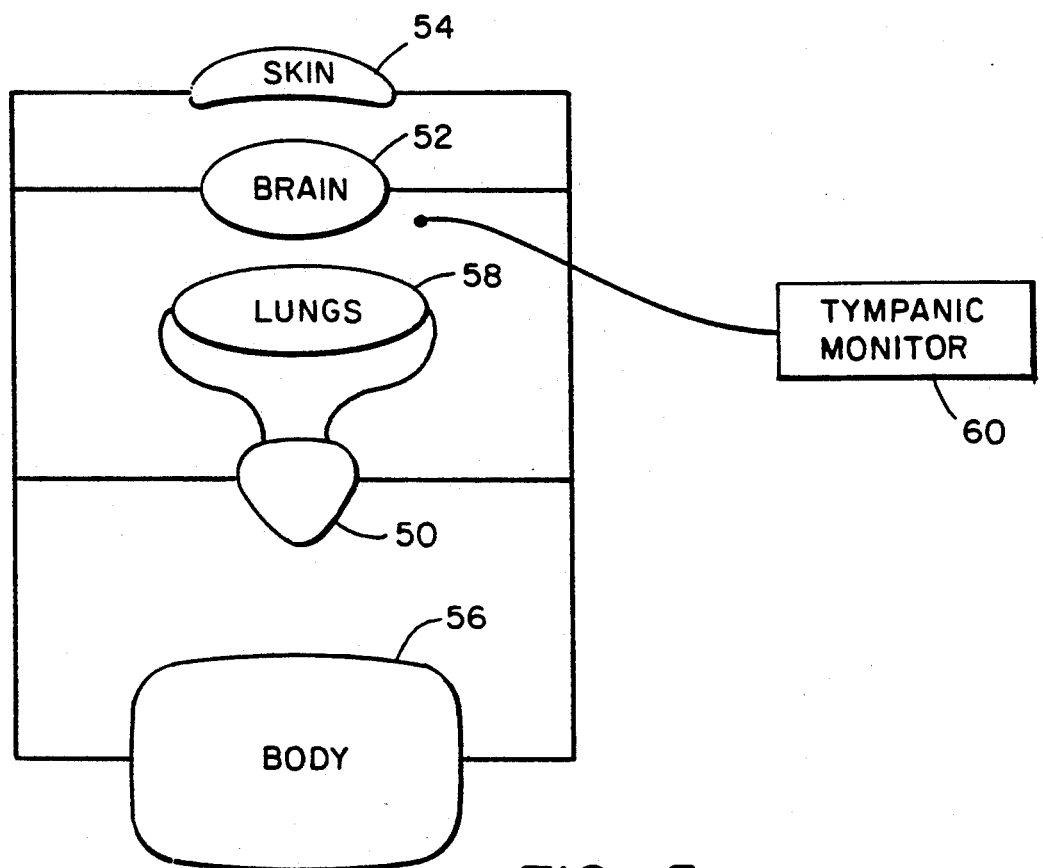
FIG. 5 illustrates a model of the human circulatory system.

A model of the human circulatory system is illustrated in FIG. 5. Blood pumped from the heart 50 is circulated through one principal loop which includes the brain 52 and, in parallel with flow through the brain, through the skin of the head and neck illustrated at 54. A second principal loop services the rest of the body illustrated at 56. Blood returning from the head and body is mixed and pumped by the heart 50 through the lungs 58 and then again through the head and body. The tissue of the head loop has only about 5% of the total mass of the body; however, about 20% of the blood flow is through the head. Thus, any heating through the skin of the head is quickly returned to the heart and lungs. With the brain, the heart and lungs are the critical organs in treating a hypothermic patient or in maintaining a patient's temperature.

Figure 6:
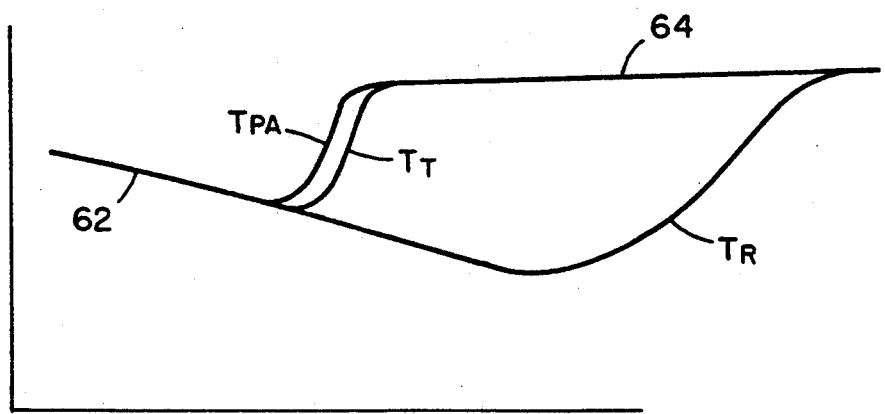
FIG. 6 illustrates changes in body temperatures with heating using the device of the present invention.

Tympanic temperature is the monitorable temperature which is closest to that of the brain. Thus, the tympanic monitor 60 provides the most critical temperature feedback. That criticality is illustrated by FIG. 6. If a patient's temperature were decreasing along the line 62 and the blood heated through the skin of the head, that heated blood would quickly reach the pulmonary artery and thus increase the temperature $T_{PA}$. Soon thereafter, the blood flow would reach the tympanic area and thus increase the tympanic temperature $T_T$. Only much later would the remainder of the body 56 increase in temperature due to the significantly lesser ratio of flow to mass. Thus a rectal temperature $T_R$ would significantly lag the tympanic temperature. With the present invention, with feedback control of the vapor source, the tympanic temperature can be clamped at a desired level 64. If one were monitoring the rectal temperature, it can be seen that the feedback system would cause excessive heat to be applied to the body even after the tympanic temperature had reached the desired level.

FIG. 5 illustrates yet another advantage of heating through the head rather than the main body. As noted, it is of primary interest that the heart, lungs and brain be properly heated. When one heats the blood through the main body 56, vaso-dilation in the body results in a greater mass of blood at the skin and thus less blood flow to the heart. When heating the skin of the head, the skin vessels present a much lower mass even with dilation. Thus, there is little remote storage of heated blood and the heart and lungs are promptly warmed.

Figure 7:
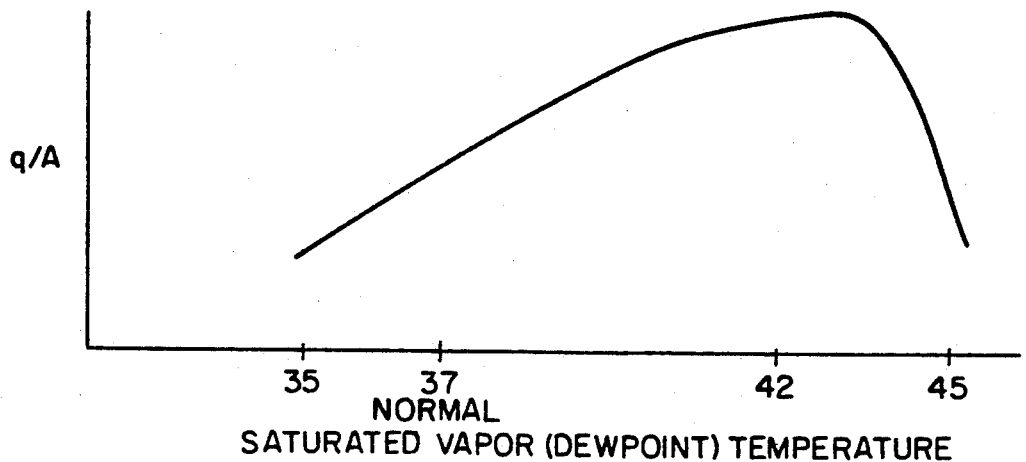
FIG. 7 illustrates change in heat transfer with change in tympanic temperature.

To maximize heat flow to the blood, the blood flow rate should be maximized. That flow rate is controlled to a large extent by the local skin temperature. As illustrated in FIG. 7, as saturated vapor temperature increases to about 42° C., blood flow and thus the heat transfer per unit area increases. However, when the saturated vapor temperature exceeds about 42° C. the body initiates a defense mechanism to minimize injury due to excessive heat. Above that temperature, vasoconstriction substantially reduces blood flow and thus heat transfer. Thus, not only is it desirable to maintain a vapor dew point temperature of less than 43° C. to avoid injury, to maximize heat transfer it is preferred that the temperature be about 42° C.

Wherein the present invention has been shown with reference to the preferred embodiments thereof, it will be understood by those skilled in the art that various changes in form and detail may be made without departing from the spirit and scope of the invention as defined in the appended claims. For example, the embodiment of FIG. 4A can be readily modified to provide cooling of a patient. In that case, a fine spray of cool water would be sprayed on the forehead and air would be blown on the forehead to evaporate the cool water.

I claim:

1. A method of quickly and safely raising a patient's body temperature, comprising the steps of:
   a) enclosing a portion of the patient's head with an enclosure which does not enclose the patient's mouth or nostrils so that the portion of the patient's head is isolated from an external environment;
   b) generating heated vapor having a dew point temperature less than 47° C. and greater than tympanic temperature of the patient; and
   c) inputting the heated vapor to the enclosure so that the heated vapor condenses on the portion of the patient's body that is isolated and raises the patient's body temperature; and
   d) monitoring the patient's temperature and controlling the heated vapor to reduce heat transfer to the patient as desired patient temperature is obtained.

2. A method as recited in claim 1 wherein step (d) comprises monitoring the patient's tympanic temperature and controlling the heated vapor to maintain a desired patient temperature.

3. A method as recited in claim 1 wherein the vapor is a mixture of water vapor and air.

4. A method as recited in claim 1 wherein the vapor dew point temperature is maintained at about 42° C.

5. A method as recited in claim 1 wherein the heated vapor is carried by gas in a nearly saturated mixture.

6. A method of maintaining patient body temperature, comprising the steps of:
   a) surrounding a portion of the patient's head with heated vapor of dew point temperature less than 47° C. and greater than 30° C., said vapor being held around the patient's head by an enclosure, the portion of the patient's head surrounded with heated vapor being exclusive of the patient's mouth and nostrils;
   b) monitoring the patient's temperature; and
   c) adjusting the vapor supply quantity or dew point temperature around the patient's head in response to the monitored temperature to reduce heat transfer to the patient as desired patient temperature is obtained.

7. A method as recited in claim 6 further comprising the step of venting excess heated vapor from the enclosure.

8. A method as recited in claim 7 further comprising collecting condensate in absorbent material retained external to the patient at the patient's head.

9. A method as recited in claim 6 wherein the vapor dew point temperature is maintained at about 42° C.

10. A method as recited in claim 6 wherein the heated vapor is carried by gas in a nearly saturated mixture.

11. A method of maintaining patient body temperature comprising the steps of:
    surrounding a portion of the patient's head with a temperature control fluid of heated vapor, said vapor being held around the patient's head by an enclosure, the portion of the patient's head surrounded with heated vapor being exclusive of the patient's mouth and nostrils;
    monitoring the patient's tympanic temperature; and
    adjusting the temperature control fluid in response to the monitored temperature to reduce heat transfer to the patient as a desired patient temperature is obtained.

12. A method as recited in claim 11 wherein the vapor dew point temperature is maintained at about 42° C.

13. A method as recited in claim 11 wherein the heated vapor has a dew point temperature less than 47° C. and greater than tympanic temperature of the patient and is carried by gas in a near saturated mixture.

14. A method of quickly and safely raising a patient's body temperature, comprising the steps of:
    a) enclosing a portion of the patient's head with an enclosure which does not enclose the patient's mouth or nostrils so that the portion of the patient's head is isolated from an external environment;
    b) generating heated vapor having a dew point temperature less than 47° C. and greater than tympanic temperature of the patient;
    c) inputting the heated vapor to the enclosure so that the heated vapor condenses on the portion of the patient's body that is isolated and raises the patient's body temperature; and
    d) monitoring the patient's temperature and controlling the heated vapor to maintain a desired patient temperature.

15. A method of quickly and safely raising a patient's body temperature, comprising the steps of:
    a) enclosing a portion of the patient's head with an enclosure which does not enclose the patient's mouth or nostrils so that the portion of the patient's head is isolated from an external environment;
    b) generating heated vapor having a dew point temperature less than 47° C. and greater than tympanic temperature of the patient;
    c) inputting the heated vapor to the enclosure so that the heated vapor condenses on the portion of the patient's body that is located and raises the patient's body temperature; and
    d) collecting condensate in absorbent material retained external to the patient at the patient's head.

16. A method of raising a patient's body temperature comprising the steps of:
    enclosing a portion of the patient's body with an enclosure which does not enclose the patient's mouth or nostrils so that the portion of the patient's body is isolated from an external environment;

generating heated vapor having a dew point temperature less than 47° C. and greater than tympanic temperature of the patient;

inputting the heated vapor to the enclosure so that the heated vapor condenses on the portion of the patient's body that is isolated and raises the patient's body temperature; and monitoring the patient's temperature and controlling the heated vapor mixture to reduce heat transfer to the patient as a desired patient temperature is obtained.

17. A method as recited in claim 16 wherein the heated vapor is carried by gas in a nearly saturated mixture.

18. A method as recited in claim 17 wherein the vapor dew point temperature is maintained at about 42° C.

19. A method as recited in claim 16 wherein the patient's temperature is monitored by measuring tympanic temperature.

* * * * *